United States Patent [19]

Steel

[11] Patent Number: 5,026,773

[45] Date of Patent: * Jun. 25, 1991

[54] APPARATUS FOR A SOLID PHASE SYNTHESIS OF PEPTIDE ANALOGS

[76] Inventor: Samuel Steel, 3817 Davis Pl., Apt. 6, Washington, D.C. 20007

[*] Notice: The portion of the term of this patent subsequent to Dec. 27, 2005 has been disclaimed.

[21] Appl. No.: 280,023

[22] Filed: Dec. 5, 1988

Related U.S. Application Data

[63] Continuation of Ser. No. 24,602, Mar. 11, 1987, Pat. No. 4,794,150.

[51] Int. Cl.$^5$ .................... C08F 283/00; C08G 63/48; C08G 63/91
[52] U.S. Cl. ................... 525/54.11; 530/333; 530/334; 422/131; 422/134
[58] Field of Search ............ 525/54.1, 54.11; 530/333, 334; 422/131, 134

[56] References Cited

U.S. PATENT DOCUMENTS

| | | | |
|---|---|---|---|
| 4,517,338 | 5/1985 | Urdea et al. | 525/54.1 |
| 4,552,922 | 11/1985 | Patchornik et al. | 525/54.1 |
| 4,746,490 | 5/1988 | Saneii | 525/54.11 |
| 4,764,595 | 8/1988 | Getman et al. | 530/334 |
| 4,794,150 | 12/1988 | Steel | 525/54.11 |

Primary Examiner—Nathan M. Nutter
Attorney, Agent, or Firm—Edwin D. Schindler

[57] ABSTRACT

A novel polymeric disc, wafer or similarly shaped resin for carrying out the synthesis of peptide analogs via solid phase peptide synthesis techniques is provided. The polymeric disc or wafer of the invention may be made out of those resin materials presently used in bead form in solid phase peptide synthesis, such as, benzhydrylamine resins, Boc-aminoacyl-4-(oxymethyl)-phenyacetamidomethyl (Pam) resin, polyamide resins and chloromethyl resins. The disc or wafer of the invention should, preferably, have a thickness of 200–400 µm and may be of any suitable length or width. A process for the synthesis of peptide analogs utilizing the polymeric disc or wafer of the present invention is also disclosed.

4 Claims, 1 Drawing Sheet

APPARATUS FOR A SOLID PHASE SYNTHESIS OF PEPTIDE ANALOGS

This application is a continuation of application Ser. No. 024,602, filed Mar. 11, 1987, now U.S. Pat. No. 4,794,150.

BACKGROUND OF THE INVENTION

1. Technical Field of the Invention

The present invention relates to the synthesis of peptide analogs. More particularly, the invention relates to a novel polymeric disc, wafer or other similarly shaped resin and a method for its use in solid phase peptide synthesis ("SPPS").

The present invention permits the rapid production of peptide analogs, i.e., numerous peptides differing from one another by only a single amino acid or a small number of amino acids. The synthesis of analogs according to the present invention can take place at a rapid rate while assuring that the reagents necessary to synthesize the analogs undergo quantitatively complete reactions so as to minimize undesirable side-reaction products which could result in the production of "deletion peptides" or "deletion sequences."

Within recent years, new hormones, releasing factors, inhibitors, growth factors, toxins, ion carriers and antibiotics have been discovered. This and related activity has created an increased need for the chemical synthesis of peptides and small proteins. Synthetic peptide analogs are essential for structure-function studies designed to investigate the mechanism of action and to produce inhibitors or superagonists of improved selectivity and duration of action. The synthesis of immunogenic peptides has great potential for the development of vaccines and can play an important role in the detection and isolation of new gene products. The present invention greatly simplifies and increases the efficiency of the task of preparing synthesis peptides.

2. Description of the Prior Art

Solid phase peptide synthesis was introduced by Dr. R. Bruce Merrifield in 1963 when Dr. Merrifield attached a growing peptide chain to a solid support. Merrifield, R. B. (1963) *J. Am. Chem. Soc.* 85, 2149-2154. The procedures enunciated by Dr. Merrifield for SPPS were as follows: An amino acid corresponding to the C-terminal of the target peptide is covalently attached to an insoluble polymeric support (the "resin"). The next amino acid, with a protected α-amino acid, is activated and reacted with the resin-bound amino acid to yield an amino protected dipeptide on the resin. Excess reactants and co-products are removed by filtration and washing. The amino-protecting group is removed and chain extension is continued with the third and subsequent protected amino acids. After the target protected peptide chain has been built up in this stepwise fashion, all side chain groups are removed and the anchoring bond between the peptide and the resin is cleaved by suitable chemical means thereby releasing the crude peptide product into solution. The desired peptide then undergoes an extensive purification procedure and is then characterized. Kent, S. & Clark-Lewis, I., "Modern Methods for the Chemical Synthesis of Biologically Active Peptides," Division of Biology 147-75, California Institute of Technology, Pasadena, Calif. 91125 U.S.A.; Houghten, R. A., Chang, W. C. & Li, C. H. (1980), *Int. J. Pept. Protein Res.*, 16, 311-320; Houghten, R. A., Ostresh, J. M. & Klipstein, F. A. (1984), *Eur. J Biochem.*, 145, 157-162; Stewart, J. M. & Young, J. D., *Solid Phase Peptide Synthesis*, Pierce Chemical Company (2d ed. 1984). See, also, Geysen, H. M., Meloen, R. H. & Barteling, S. J. (1984) *Proc. Natl. Acad. Sci. USA*, 81, 3998-4002; Matthes, H. W. D., Zenke, W. M., Grundstrom, T., Staub, A., Wintzerith, M. & Chambon P., (1984) *The EMBO Journal*, 3, 801-805.

The resin employed in standard SPPS is known as the "Merrifield resin" and is a polystyrene bead of 100-200 microns in size. The resin typically contains 0.5-2.0% divinylbenzene cross-linkage and contains 0.2 to 0.8 mmole of p-chloromethyl groups per gram resin. The number of p-chloromethyl groups determines the number of individual chains per gram and their ultimate size. The size of the bead allows for a rapid penetration of reagents in SPPS. The percentage of cross-linkage determines the extent to which the resin shrinks and swells during solvent changes. A large shrink-and-swell effect is preferred.

Dr. Merrifield had adopted known techniques of peptide chemistry, which were being used by others in solution phase peptide synthesis, for solid phase peptide synthesis. In doing so, Dr. Merrifield eliminated the intensive purification procedures required between each chemical step; the solid-phase procedure only required filtration and rinsing of the solid support with fresh solvent. Solid phase synthesis permitted chemists to add 5-6 amino acids per day rather than one or two amino acids per week.

While the solid phase technique had revolutionized biomedical research in industry and academia, this procedure has remained essentially unchanged since its inception in the early 1960's. With the explosive pace at which biotechnical research has been advancing in the industralized nations of the world, substantially more peptides, particularly analogs, of greater complexity are needed in industry and research than ever before.

The ever increasing demand for analog peptides has been approached in several ways, but no approach, thus far, has proven completely satisfactory. One highly expensive and labor intensive method has been to use a series of reaction vessels, e.g., Stewart, J. M. & Young, J. D., *Solid Phase Peptide Synthesis*, Pierce Chemical Company, pp. 125-130 (2d ed. 1984), rather than use of a single reaction vessel.

Thereafter, the "pin" method was developed which resulted in the synthesis of peptides on the surface of a dowel rod. The concept was to employ many rods along a plate with each rod entering a different reaction well. The drawbacks inherent in the pin method are multi-fold. First, the formed peptide remains on the dowel during biological testing; there is no guarantee that the conformation of the bound peptide duplicate the conformation in solution. Secondly, and more importantly, each analog in actuality represented a separate synthesis. Accordingly, if one dowel were to show a superior biological response, there would be no means of determining whether the reactions involved in the synthesis of a particular analog was superior or whether an analog synthesized was biologically superior.

Subsequent to the pin method, the "tea bag" method was developed where a resin was placed in individual packets similar in design to ordinary tea bags. See, Houghten, R. A., (1985) *Proc. Natl. Acad. Sci. USA* 82, 5131-5135. The concept of the tea bag method was that many tea bags could be placed into the same reaction vessel so that many peptides could be synthesized together. When the point of difference or deviation was reached in the formation of particular peptides, i.e., the point where an analog would differ from a similar peptide by a single or small number of amino acids, each tea bag would be separated by hand and reacted separately for the differing amino acids. Following the necessary separate reactions, the tea bags would all be returned to the same reaction vessel for the continued formation of those portions of the analogs which would be common to several peptides, thereby minimizing experimental error. Theoretically and initially, the tea bag method appeared to be ideal. In practice, however, the tea bag mesh would necessarily be prohibitively small. The flow of reagents to the resin would be inhibited. Consequently, many reactions would fail to go to completion thereby resulting in the synthesis of peptides having deletion sequences. The resulting truncated peptides could not, without possibly great difficulty, be separated from analog peptides having the proper sequence.

SUMMARY OF THE INVENTION

In accordance with the present invention, provided is a novel polymeric disc, wafer or similarly shaped resin for carrying out the synthesis of peptide analogs via the solid phase peptide synthesis techniques generally known and described above. The polymeric disc of the present invention may be made out of those resins presently used in bead form in SPPS, such as, for example, benzhydrylamine resins, e.g., p-methylbenzhydrylamine (MBHA) resin, Boc-aminoacyl-4-(oxymethyl)-phenylacetamidomethyl (Pam) resin, polyamide resins and chloromethyl resin materials (the "classical Merrifield" resin), among others. If the disc is made of crosslinked polystyrene, preferably there would be a 2–5% cross-linkage.

The inventive polymeric disc, which it will be understood as including all suitably shaped and sized resins, not merely that which may be thought of as a circular disc, should be sufficiently thin so as to allow for the rapid penetration of reagents to insure that the required reactions may run to completion. The disc of the invention should, preferably, have a thickness of 200–400 μm. Aside from this parameter, i.e., the thickness of the disc, the precise shape of the disc, it should be emphasized, may be any shape having any suitable length or width whatsoever depending upon the requirements of the user.

As part of the present invention, a process for the synthesis of peptide analogs, using the polymeric resin disc of the invention is further disclosed.

BRIEF DESCRIPTION OF THE DRAWING

In the Drawing:

The FIG. 1 outlines the experimental process of solid phase peptide synthesis.

DETAILED DESCRIPTION OF THE PREFERRED EMBODIMENTS

Figure 1:
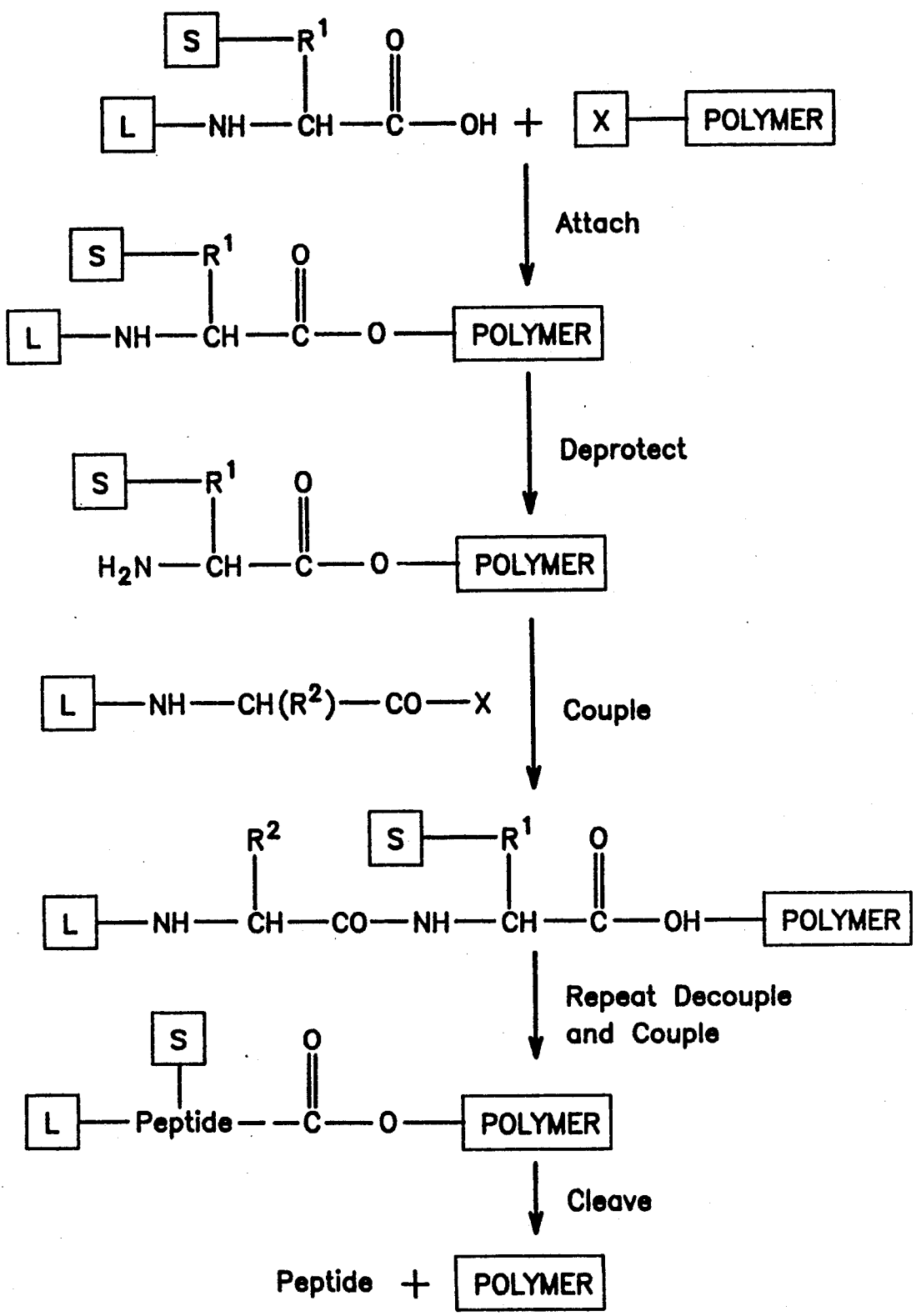

The concept of solid phase peptide synthesis and, as will be explained, as it relates to the present invention may best be understood by reference to the experimental procedure outlined in FIG. 1, wherein X is a reactive group, such as a p-chloromethyl group; L is a labile protecting group; and S is a stable side-chain blocking group to prevent side chain reactions during the peptide synthesis.

Referring to FIG. 1, a synthetic polymer, such as the polymeric disc of the present invention, would bear reactive groups, X. The amino acid which will form the C-terminal residue of the peptide to be synthesized is converted to a derivative in which its amino acid group is protected by a labile protecting group, L. Any standard protecting group, such as, for example, the Boc group, may be used in conjunction with the present invention. The foregoing derivative of the C-terminal amino acid is coupled to the reactive polymer. At this point, the repetitive cyclic part of SPPS begins. A reagent is applied to the protected aminoacyl polymer to remove the labile blocking group, L, from the amino acid residue. The reagent employed must not, in any way, harm the link of the C-terminal residue to the polymer. Moreover, if the amino acid attached to the polymer (and all amino acids in the peptide to be synthesized) contains a side-chain reactive functional group, that functional group must be blocked by a stable blocking group, S, which will remain completely intact throughout the synthesis, but which can be removed finally to yield the free peptide. Following removal of the labile protecting group, the next amino acid is coupled to the aminoacyl polymer by use of a suitable coupling reaction. Again, the α-amino group must be protected with the labile group.

This cycle of deprotection and coupling is then repeated with each amino acid which is to be incorporated into the peptide chain. For the deprotection reaction, standard acidolysi methods, such as, a 25% solution of trifluoroacetic acid in dichloromethane may be used. Dicyclohexyl-carbodiimide (DCC) may be employed as the coupling agent, as well as other suitable coupling agents for use with the present invention. Finally, after the entire blocked peptide has been assembled on the polymer support, such as the present invention, a different type of reagent, e.g., anhydrous liquid hydrogen fluoride, is applied to cleave the peptide from the polymer and allow it to be dissolved. The blocking groups, which have protected side-chain functional groups, must also be removed, and are usually chosen so that they can be removed simultaneously with the cleavage of the peptide from the resin. The peptide can also be cleaved from the resin by ammonia and amines to yield peptide amides.

The present invention concerns the polymer support to be employed in the foregoing SPPS framework. The support must be insoluble and have satisfactory means of attaching the first amino acid to it. The polymeric disc of the present invention, i.e., the polymer support, may be made out of those resin materials presently used for SPPS when such is carried out with fine bead resins via conventional means. The polymeric disc, which may have any desired shape suitable for the user (e.g., any suitable length or width) should, preferably, have a thickness of 200–400 μm. The resin of the present invention may be made out of, for example, a benzhydrylamine, e.g., p-methylbenzhydrylamine, Boc-aminoacyl-4-(oxymethyl)-phenylacetamidomethyl (Pam), polyamide, p-hydroxymethyl resin, "Wang" resins (e.g., hydrazide resin, ether resin, p-alkoxybenzyl alcohol resin), and cross-lined polystyrene, among other materials. Wang, S. S., *J. Am. Chem. Soc.* 43, 1328–43 (1973). If cross-linked polystyrene is to be the material of the resin, the composition of the resin should be at least 1% divinylbenzene; would be too fragile to be of any use to the chemist.

Additionally, the inventive resin, to be effective, need not rely upon permeation, but may effectively act via a surface reaction. Thus, a hybrid-type resin is possible. Such a hybrid resin may have a strong, inert support, or backing, made of, for example, plastics or nylons (e.g., Nylon-66), or other materials.

The present invention further includes a method for use of the novel polymeric disc. In the synthesis of analogs, discs would be individually tagged. Peptide synthesis upon the severally tagged discs would take place within one reaction vessel in accordance with known principles of SPPS. When the point of deviation in the peptides is reached, i.e., where the amino acid or acids which are to differ from one peptide analog to another in the synthesis process is reached, the discs of the invention can be separated by hand or other procedure, (e.g., tongs) reacted separately in different reaction vessels and then, subsequently, again placed in the same reaction vessel to continue or complete the synthesis of the analog chain with those amino acids generally common to the peptide analogs. Unlike prior methods, such as the tea bag method, where the bag mesh is too dense to allow for proper permeation, the present invention permits the necessary reactions to run to completion.

Finally, a hybrid-type resin, having an inert support as described above, which relies upon a surface reaction, can also be conveniently transferred between reaction vessels with conventional tongs.

The invention will now be more fully described by reference to the following Example. It should, however, be understood that the following Example is for purposes of illustration only and not meant for the purpose of defining the limits or scope of the invention.

EXAMPLE

The following procedure is suggested for the synthesis of the following three analogs of enkephalin:

| (1) Tyr—Gly—Gly—phe—Leu | (Natural) |
| (2) Tyr—DAla—Gly—phe—Leu | [D—Ala²] Enkephalin |
| (3) Tyr—Gly—Gly—DPhe—Leu | [D—Phe⁴] Enkephalin |

Step 1: Place three 4"×4" polymeric discs of the present invention into a flat glass reaction tank.

Step 2: Rinse the discs as follows:
2×100 ml of dichloromethane for 5 minutes each; and
2×100 ml of dimethylformamide for 5 minutes each.

Step 3: Add 1:1 molar ratio of Boc-amino acid cesium salt [(Boc-Leu-O⁻)$_2$Cs$^{+2}$] to the discs containing p-chloromethyl groups overnight in a water bath at 50° C.

Step 4: Rinse the discs of the invention in the following solvents:
2×100 ml dimethylformamide for 2 minutes each
2×100 ml dimethylformamide:H$_2$O (1:1) for 2 minutes each
2×100 ml dimethylformamide for 2 minutes each
2×100 ml methanol for 2 minutes each
3×100 ml dichloromethane for 2 minutes each Step 5: Deprotect with 100 ml of 45% trifluoroacetic acid in dichloromethane for 20-30 minutes.

Step 6: Rinse off trifluoroacetic acid with 6×100 ml washes of dichloromethane, 2 minutes each.

Step 7: Neutralize discs with 2×100 ml washes of 10% triethylamine in dichloromethane, 2 minutes each.

Step 8: Rinse off triethylamine with 6×100 ml washes of dichloromethane, 2 minutes each.

Step 9: Remove disc #3 and place into a second tank or reaction vessel.

Step 10: Add 3 molar excess of Boc-DPhe-OH to discs #1 and #2 (6 moles total) in dichloromethane; and
Add 3 molar excess of Boc-DPhe-OH to disc #3 (3 moles total) in dichloromethane.

Step 11: Add 6 moles dicyclohexylcarbodiimide in dichloromethane to discs #1 and #2; and
Add 3 moles to disc #3.

Step 12: React for 1 hour, rinse with 6×100 ml dichloromethane 2 minutes each.

Step 13: Repeat Steps 7, 8, 10, 11 and 12.

Step 14: Deprotect by placing all three discs together in 45% trifluoroacetic acid/dichloromethane for 30 minutes.

Step 15: Rinse 6×100 ml dichloromethane.

Step 16: Neutralize as in Step 7.

Step 17: Rinse 6×100 ml dichloromethane.

Step 18: Add 9 moles total of Boc-Gly-OH and 9 moles of dicyclohexylcarbodiimide in dichloromethane.

Step 19: React 1 hour and rinse with 6×100 ml dichloromethane

Step 20: Neutralize and rinse.

Step 21: Repeat Steps 18 and 19.

Step 22: Deblock (as in Step 14) and rinse (as in Step 15).

Step 23 Neutralize and rinse.

Step 24 Remove disc #2 and place into a second tank (reaction vessel).

Step 25: Add 6 moles of Boc-Gly-OH and 6 moles dicyclohexylcarbodiimide in dichloromethane to discs #1 and #3; and
Add 3 moles of Boc-DAla-OH and 3 moles of dicyclohexylcarbodiimide to disc #2.

Step 26: React 1 hour and rinse discs.

Step 27: Neutralize and rinse.

Step 28: Repeat Steps 25 and 26.

Step 29: Place all three discs together, deprotect and rinse.

Step 30: Neutralize the discs and rinse.

Step 31: React with 9 moles of Boc-Tyr-OH and dicyclohexylcarbodiimide in dichloromethane for 1 hour.

Step 32: Rinse, neutralize, rinse and repeat Step 31.

Step 33: Rinse, deprotect and rinse.

Step 34: Rinse 2×100 ml methanol (2 minutes each).

Step 35: Dry, preferably, under vacuum.

Step 36: Cleave each disc using 90% hydrogen fluoride and 10% anisole for 1 hour at 0 degrees C., then evaporate hydrogen fluoride with vacuum at 0 degrees C.

Step 37: Extract anisole residue with 3×50 ml diethyl ether.

Step 38: Extract peptide from residue using 1%, 10% and 50% AcOH.

Step 39: Lyophilize peptide.

While only several embodiments of the present invention have been shown and described, it will be obvious to those skilled in the art that many modifications may be made thereunto without departing from the spirit and scope of the invention.

What is claimed is:

1. Apparatus for a solid phase peptide synthesis of peptide analogs, comprising:
a polymeric resin being insoluble and capable of permitting an attachment to it of a first amino acid in said solid phase peptide synthesis wherein said polymeric resin includes an inert support which is capable of permitting a transfer of said polymeric resin from a first reaction vessel to a second reaction vessel by means of a tongs instrument; and, reactor cell means for use in combination with said polymeric resin, said reactor cell means including a plurality of reaction vessels wherein at least one of said reaction vessels of said reactor cell means is capable of at least partially containing a plurality of said polymeric resins during said solid phase peptide synthesis, said polymeric resin being suitably shaped and sized for use in combination with said reactor cell means wherein said polymeric resin is not separately contained in a foraminous container within said reactor cell means which would be capable of inhibiting the flow of reagents to said polymeric resin.

2. Apparatus for a solid phase peptide synthesis according to claim 1, wherein said polymeric resin is made of a member selected from the group consisting of a benzhydrylamine, Boc-aminoacyl-4-(oxymethyl)-phenylacetamidomethyl, polyamide, cross-linked polystyrene, p-hydroxymethyl, hydrazide, ether, p-alkoxybenzyl alcohol and a combination thereof.

3. Apparatus for a solid phase peptide synthesis according to claim 1, wherein said polymeric resin includes an inert support.

4. Apparatus for a solid phase peptide synthesis according to claim 3, wherein said inert support is a nylon.

* * * * *